United States Patent
Wang et al.

(10) Patent No.: US 10,893,796 B2
(45) Date of Patent: Jan. 19, 2021

(54) 2D MULTI-LAYER THICKNESS MEASUREMENT

(71) Applicant: Topcon Corporation, Tokyo (JP)

(72) Inventors: Zhenguo Wang, Ridgewood, NJ (US); Zaixing Mao, Harrison, NJ (US); Kinpui Chan, Ridgewood, NJ (US)

(73) Assignee: TOPCON CORPORATION, Tokyo (JP)

( * ) Notice: Subject to any disclaimer, the term of this patent is extended or adjusted under 35 U.S.C. 154(b) by 180 days.

(21) Appl. No.: 16/252,818

(22) Filed: Jan. 21, 2019

(65) Prior Publication Data

US 2019/0231187 A1 Aug. 1, 2019

Related U.S. Application Data

(60) Provisional application No. 62/622,544, filed on Jan. 26, 2018.

(51) Int. Cl.
| | |
|---|---|
| *A61B 3/10* | (2006.01) |
| *G01B 11/06* | (2006.01) |
| *G06T 7/00* | (2017.01) |
| *G06T 11/60* | (2006.01) |
| *A61B 3/14* | (2006.01) |
| *A61B 5/00* | (2006.01) |
| *A61B 5/107* | (2006.01) |

(52) U.S. Cl.
CPC ............ *A61B 3/101* (2013.01); *A61B 3/1005* (2013.01); *A61B 3/14* (2013.01); *A61B 5/0075* (2013.01); *G01B 11/06* (2013.01); *G01B 11/0633* (2013.01); *G06T 7/0012* (2013.01); *G06T 11/60* (2013.01); *A61B 5/1075* (2013.01); *G06T 2207/30041* (2013.01)

(58) Field of Classification Search
CPC .. A61B 3/102; A61B 3/14; A61B 3/12; A61B 3/0008; A61B 3/1005; A61B 3/107; A61B 3/101
USPC ................ 351/221, 212, 206, 205, 200, 246
See application file for complete search history.

(56) References Cited

U.S. PATENT DOCUMENTS

| | | | |
|---|---|---|---|
| 5,486,701 A | 1/1996 | Norton et al. | |
| 5,640,242 A | 6/1997 | O'Boyle et al. | |
| 8,215,774 B2 | 7/2012 | Korb et al. | |
| 8,256,898 B2 | 9/2012 | Gratton et al. | |

(Continued)

FOREIGN PATENT DOCUMENTS

| | | |
|---|---|---|
| EP | 3113668 A2 | 1/2017 |
| WO | 2015132788 A2 | 9/2015 |

OTHER PUBLICATIONS

M.G. Moharam et al., "Stable implementation of the rigorous coupled-wave analysis for surface-relief gratings: enhanced transmittance matrix approach", J. Opt. Soc. Am. A, vol. 12, No. 5 (1995), pp. 1077-1086.

(Continued)

*Primary Examiner* — Hung X Dang
(74) *Attorney, Agent, or Firm* — Pearne & Gordon LLP

(57) ABSTRACT

A method for measuring layer thicknesses of a multi-layer structure includes generating first and second 2D images of the structure, each image being generated by measuring an intensity of a reflection of incident lights, from different discrete narrow spectral bands, on the structure. Thicknesses for at least one layer of the structure are then determined based on the measured reflection intensities at those locations.

21 Claims, 12 Drawing Sheets

(56) References Cited

U.S. PATENT DOCUMENTS

| | | | |
|---|---|---|---|
| 9,028,065 B2 | 5/2015 | Yokoi et al. | |
| 9,696,134 B2 | 7/2017 | Arieli et al. | |
| 2010/0315591 A1* | 12/2010 | Gratton et al. | A61B 3/101 351/206 |
| 2013/0050648 A1 | 2/2013 | Steinmueller | |

OTHER PUBLICATIONS

T.J. Lieznerksi et al., "Analysis of Shearing Interferograms of Tear Film Using Fast Fourier Transforms", J. of Biomedical Optics, vol. 3 No. 1, (1998), pp. 32-37.

N. Fogt and P. E. King-Smith, "Interferometric measurement of tear film thickness by use of spectral oscillations", J. Opt. Soc. Am. A, vol. 15, No. 1 (1998), pp. 268-275.

A. Khamene et al., "A Spectral-Discrimination Method for Tear-Film Lipid-Layer Thickness Estimation from Fringe Pattern Images", IEEE Transactions on Biomedical Engineering, vol. 47, No. 2, Jan. 1, 2000 (Jan. 1, 2000), XP011006833, ISSN: 0018-9294, pp. 249-258.

P. E. King-Smith et al., "Inteiferometric imaging of the full thickness of the precorneal tear film", J. Opt. Soc. Am. A, vol. 23, No. 9 (2006), pp. 2097-2104.

K. Azartash et al., "Non-invasive in vivo measurement of the tear film using spatial autocorrelation in a live mammal model", Biomedical Optics Express, vol. 1, No. 4 (2010), pp. 1127-1137.

B. Remeseiro et al. "Statistical Comparison of Classifiers Applied to the Interferential Tear Film Lipid Layer Automatic Classification", Computational and Mathematical Methods in Medicine, (2012), pp. 1-10.

J. Huang et al., "Maximum-likelihood estimation in Optical Coherence Tomography in the context of the tear film dynamics", Biomedical Optics Express, vol. 4, No. 10 (2013), pp. 1806-1816.

M. M. Bartuzel et al., "Automatic dynamic tear meniscus measurement in optical coherence tomography", Biomedical Optics Express, vol. 5, No. 8 (2014), pp. 2759-2768.

J. Huang et al. "Measurement of a multi-layered tear film phantom using optical coherence tomography and statistical decision theory", Biomedical Optics Express, vol. 5, No. 12 (2014), pp. 4374-4386.

J. Huang et al. "Simultaneous measurement of lipid and aqueous layers of tear film using optical coherence tomography and statistical decision theory", Proceedings of SPIE 8936, Design and Quality for Biomedical Technologies VII, 89360A (2014).

H. Lu et al., "Tear film measurement by optical reflectometry technique", J. of Biomedical Optics, vol. 19, No. 2 (2014).

V. Aranha Dos Santos et al., "In vivo tear film thickness measurement and tear film dynamics visualization using spectral domain optical coherence tomography", Optics Express, vol. 23, No. 16 (2015), pp. 21043-21063.

J. Huang et al., "In vivo thickness dynamics measurement of tear film lipid and aqueous layers with optical coherence tomography and maximum-likelihood estimation", Optics Letters, vol. 41, No. 9 (2016), pp. 1981-1984.

V. Aranha Dos Santos et al., "Super-resolved thickness maps of thin film phantoms and in vivo visualization of tear film lipid layer using OCT", Biomedical Optics Express, vol. 7, No. 7 (2016) pp. 2650-2670.

Donald R. Korb et al., "Tear Film Lipid Layer Thickness as a Function of Blinking", Cornea, 13(4):pp. 354-359, 1994.

Eiki Goto, et al., "Computer-synthesis of an interference color chart of human tear lipid layer, by a colorimetric approach, Investigative ophthalmology & visual science", Nov. 2003, vol. 44, No. 11, pp. 4693-4697.

Hyeonha Hwang, et al., "Image-based quantitative analysis of tear film lipid layer thickness for meibomian gland evaluation" BioMedical Engineering OnLine, 2017, 16:135, DOI 10.1186/s12938-017-0426-8, pp. 1-15.

P. Ewen King-Smith, et al. "Three Interferometric Methods for Measuring the Thickness of Layers of the Tear Film", Optometry and Vision Science, 1040-5488/99/7601-0019/0, Jan. 1999, vol. 76, No. 1, pp. 19-32.

P. Ewen King-Smith, et al., "The thickness of the human precorneal tear film: evidence from reflection spectra", Investigative Ophtalmology & Visual Science, Oct. 2000, vol. 41, No. 11, pp. 3348-3359.

Jason J. Nichols and P. Ewen King Smith, "Thickness of the Pre- and Post—Contact Lens Tear Film Measured In Vivo by Interferometry", Investigative Ophthalmology & Visual Science, Nov. 2003, vol. 44, No. 11, pp. 68-77.

Jason J. Nichols, et al., "Thinning rate of the precorneal and prelens tear films", Investigative Ophthalmoolgy & Visual Science, Jul. 2005, vol. 46, No. 7, pp. 2353-2361.

P. Ewen King-Smith, et al., "Application of a novel interferometric method to investigate the relation between lipid layer thickness and tear film thinning", Investigative Ophthalmoolgy & Visual Science, May 2018, vol. 51, No. 5, pp. 2418-2423.

Jianbua Wang et al., "Precorneal and Pre-and Postlens Tear Film Thickness Measured Indirectly with Optical Coherence Tomography", Investigative Ophthalmoolgy & Visual Science, Jun. 2003, vol. 44, No. 6, pp. 2524-2528.

Kaveh Azartash et al., "Pre-corneal tear film thickness in humans measured with a novel technique", Molecular Vision 2011; 17:756-767; <http://www.molvis.org/molvis/v17/a86>; Published Mar. 22, 2011.

Extended European Search Report for European Application No. 19153552.5 dated Jun. 26, 2019.

Tremmel Anton J., et al., "Inline hyperspectral thickness determination of thin films using neural networks", Proceedings of SPIE; [Proceedings of SPIE ISSN 0277-786X vol. 10524], SPIE, US, vol. 10213, Apr. 28, 2017 (Apr. 28, 2017), pp. 10213G-1-10213G-7; XP060089950, D01: 10.1117/12.2262070.

Thomas Olsen, "Reflectory of the precorneal film", Acta Opthalmologica, 63 (1985) 432-438.

* cited by examiner

Thickness Map for the Outmost Layer in a Simulated Model

Thickness Map for the Middle Layer in a Simulated Model

Reconstructed Thickness Map for the
Outmost Layer in a Simulated Model

Reconstructed Thickness Map for the
Middle Layer in a Simulated Model

2D MULTI-LAYER THICKNESS MEASUREMENT

CROSS REFERENCE TO RELATED APPLICATIONS

This application claims priority to U.S. Provisional Application Ser. No. 62/622,544, filed on Jan. 26, 2018, entitled "2D MULTI-LAYER THICKNESS MEASUREMENT", the entirety of which is incorporated herein by reference.

BACKGROUND

Dry eye has become one of the most common causes for ophthalmological doctor visits. Dry eye is a multifactorial disease of the ocular surface that is related to the tear film. As illustrated in FIG. 1, the tear film 100 comprises the outer layers of the eye including a lipid layer 102 that is about 42 nm thick, a muco-aqueous layer 104 (also referred to as a mucous and/or aqueous layer) that is about 2 µm thick, and the cornea 106, which is about 0.5 mm thick, follows the muco-aqueous layer. Currently, few technologies exist for imaging and analyzing the layers of the tear film 100 (e.g., determining layer thickness) to objectively assist dry eye diagnosis.

Interferometric techniques are among the currently available non-invasive measurements. Of these, one approach relies on the correlation between an image color and the lipid layer thickness, either quantitatively or qualitatively. Theoretically, the analysis is performed based on two-dimensional (2D) images, while typically only the average thickness within a fairly large area is presented. However, this approach is usually limited for relative lipid layer thickness estimates and may be susceptible to phase ambiguity and uncertainty in absolute thickness measurement.

More rigorous numerical analysis of the reflection spectra can be performed based on physics models using Fourier transform/least square fitting techniques. However, this typically requires a spectrometer, which limits the measurement at a single spot and makes the system design complicated and more expensive.

Optical coherence tomography (OCT) has also been used for tear film thickness measurement by combining high-end ultrahigh resolution OCT and sophisticated statistical decision theory to determine thicknesses of various layers. Theoretically, 2D measurements can be achieved with a proper scanning mechanism, but practically ultrahigh resolution OCT systems are very expensive.

Lastly, fluctuation analysis by spatial image correlation has also been applied to quantify the thickness of the pre-corneal tear film. However, this technique has still yet to demonstrate the capability for lipid layer thickness measurement.

BRIEF SUMMARY

According to a first example, a method for measuring layer thicknesses of a multi-layer structure comprises: generating a first two-dimensional (2D) image of the structure by, for each pixel of the first 2D image, measuring an intensity of a reflection of a first incident light at a location of the structure corresponding to the pixel; generating a second 2D image of the structure by, for each pixel of the second 2D image, measuring an intensity of a reflection of a second incident light at a location of the structure corresponding to the pixel; determining a thickness for at least one layer of the structure at each location of the structure based on the intensities of the measured reflections of corresponding pixels in the first and second 2D images, wherein the first incident light is generated in a first discrete narrow spectral band, the second incident light is generated in a second discrete narrow spectral band, and the first and second discrete narrow spectral bands do not fully overlap, and wherein the intensities of the reflection of the first and second incident light are measured by a light sensor.

In various embodiments of the above example, the first and second discrete narrow spectral bands are sufficiently narrow to mitigate fringe washout and preserve thickness information of the thickest layer of the structure; the multilayer structure is a tear film of an eye; the method further comprises generating additional 2D images with incident light in additional discrete narrow spectral bands, wherein a total number of narrow spectral bands is equal to or greater than a number of determined layer thicknesses; the at least one determined layer thickness is a thickness of a lipid layer or a muco-aqueous layer of a tear film of an eye; the method further comprises generating a third 2D image with incident light in a third discrete narrow spectral band, wherein the first, second, and third discrete narrow spectral bands are evenly distributed across a spectral bandwidth of measurement; the method further comprises generating a third 2D image with incident light in a third discrete narrow spectral band, wherein the first, second, and third discrete narrow spectral bands are unevenly distributed across a spectral bandwidth of measurement; the thickness for the at least one layer of the structure is determined by solving a system of equations for layer thickness of the at least one layer of the structure, and each of the equations represents a measured intensity of reflected light from incident light on the structure at wavelengths corresponding to the first and second discrete narrow spectral bands, and is further a function of indices of refraction for the at least one layer of the structure; the measured intensity of reflected light is determined according to the following equation:

$$I(\lambda) = \alpha(\lambda) - \beta(\lambda)\cos\left(\frac{4\pi n_1 d_1}{\lambda}\right) + \gamma(\lambda)\cos\left(\frac{4\pi(n_1 d_1 + n_2 d_2)}{\lambda}\right),$$

wherein λ represents wavelength within the first or second discrete narrow spectral band, α, β, and γ are predetermined factors, $n_1$ and $n_2$ are the indices of refraction for first and second layers of the structure, respectively, and $d_1$ and $d_2$ are the layer thicknesses for the first and second layers of the structure, respectively; at least one of the measured intensities is adjusted for a spectral response of an optical system that provides the first and second incident lights to the structure and light reflected by the structure to the light sensor, or for a spectral response of the light sensor; the thickness for the at least one layer of the structure is determined by solving a system of equations for layer thickness of the at least one layer of the structure, each of the equations representing a summation of measured intensities of reflected light from incident lights on the structure at wavelengths corresponding to the first and second discrete narrow spectral bands determined according to: $I_{measure}(\lambda_1, \lambda_2) = \int_{\lambda_1}^{\lambda_2} I(\lambda) E_{optics}(\lambda) E_{sensor}(\lambda)$, wherein: I(λ) is a measured intensity of reflected light for an incident wavelength of light λ, and is further a function of the layer thickness of the at least one layer of the structure, and the indices of refraction for the at least one layer of the structure, $\lambda_1$ and $\lambda_2$ are lower and upper limits for a respective one of the discrete narrow spectral bands, $E_{optics}$ is a spectral response of an optical system that provides the first and second incident lights to the structure and light reflected by the structure to the light sensor, and $E_{sensor}(\lambda)$ is a spectral response of the light sensor; the thickness for the at least one layer of the structure is determined by inputting a measured intensity of reflected light from incident light on the structure to a trained machine learning system; the machine learning system is trained in a supervised setting to output a thickness to relate a measured intensity to a layer thickness based on fully resolved spectrometric reflectance for a wavelength of incident light corresponding to the measured intensity, measurements of a physical tear film model, and/or numerical models or simulations; the locations of the structure corresponding to each pixel of the first and second 2D images are illuminated with the first incident light prior to the locations of the structure corresponding to each pixel of the first and second 2D images being illuminated with the second incident light; the location of the structure corresponding to a first pixel of the first and second 2D images is illuminated with the first incident light and the second incident light prior to the location of the structure corresponding to a second pixel being illuminated with the first incident light and the second incident light; for each location of the structure corresponding to a pixel of the first and second 2D images, the pixel location is illuminated with the first and second incident light simultaneously and the intensities of the reflections of the first and second incident lights are measured simultaneously; the first and second discrete narrow spectral bands do not overlap; and/or a bandwidth of the first discrete narrow spectral band and is different than a bandwidth of the second discrete narrow spectral band.

According to another example, an imaging system comprises a processor configured to control execution of the steps of the method of the above example and any of the associated embodiments; a light source configured to generate the first and second incident light; and the light sensor configured to measure the reflection of incident light.

In various embodiments of the example imaging system, the light source is a broadband light source or a light emitting diode; and/or the light sensor is a hyperspectral/multi-spectral camera.

DETAILED DESCRIPTION OF THE DRAWINGS

Based on the foregoing deficiencies, the present disclosure is based in part on the recognition that 'fringe' images carry thickness information for both the lipid and muco-aqueous layers of the tear film. In contrast, it has been traditionally understood that color fringes are only affected by the lipid layer, and therefore the muco-aqueous layer has been ignored when interpreting the color fringes. In view of this recognition, the present disclosure describes a method for determining thickness for both lipid and muco-aqueous layers from 2D color/multi-spectral fringe images.

Figure 1:
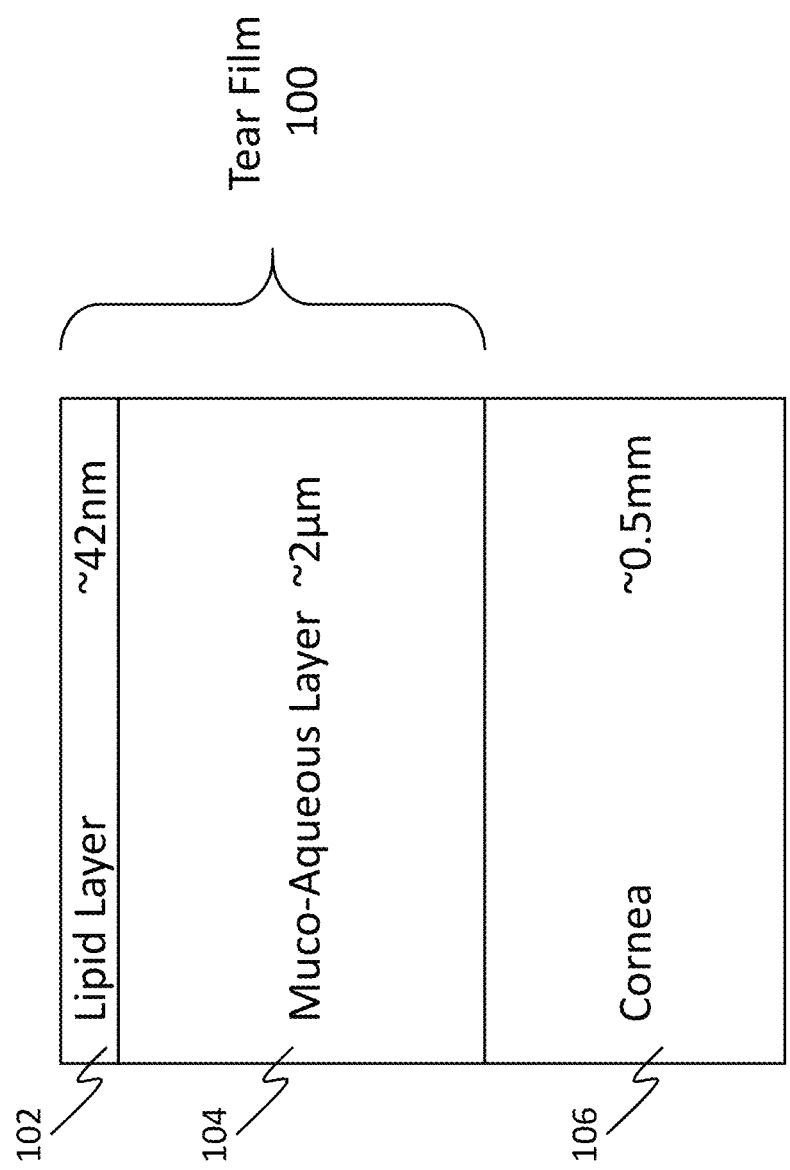
FIG. 1 schematically illustrates the layers of the tear film of the eye.
Figure 2:
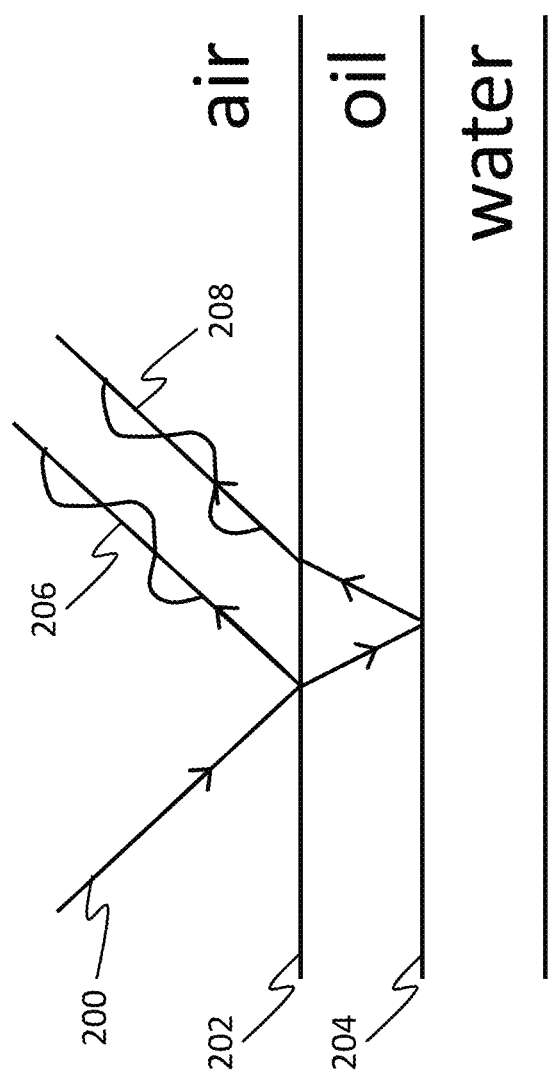
FIG. 2 illustrates the principles of transmission, reflection, and refraction of an incident light beam on a multilayer object.

Initially, it is noted that 'fringe' images are those resulting from interference among reflected light rays from an incident light beam on an imaged object. Notably, when an incident light beam (having a wavelength $\lambda$) traveling through a medium comes into contact with a boundary to another layer, a portion of that light beam is reflected while another portion is transmitted through the barrier, and refracted. If the transmitted portion comes into contact with another medium barrier, it too is partially transmitted and reflected. By way of example illustrated in FIG. 2, when an incident light beam 200 traveling through air contacts an air-oil interface 202, it is partially reflected and partially transmitted. When the transmitted portion comes in contact with an oil-water interface 204, it is reflected back toward, and transmitted through, the oil-air interface 202. As a result, two light rays 206, 208, having traveled different path lengths, are transmitted back through the air away from the air-oil interface 202.

When the path length difference between the reflected rays 206, 208 is an odd multiple of $\lambda/2$, the beams are out of phase with each other and produce destructive interference; when the path length difference between the beams 206, 208 is an even multiple of $\lambda/2$, the beams are in phase with each other and produce constructive interference. This interference can form a 'fringe' image, whereby regions of destructive interference produce a dark fringe and regions of constructive interference produce a bright fringe.

This observed interference of the reflected waves 206, 208 is dependent on four factors: the layer thicknesses, the illumination/observation angle, the refraction index of the mediums/layers, and the wavelength of incident light. With prior knowledge of refraction index of the layers of the tear film, there are three corresponding interferometric methods for studying the tear film: 1) thickness-dependent fringes, 2) angle-dependent fringes, and 3) wavelength-dependent fringes. Due to the higher tolerance for alignment error, interferometry based on wavelength-dependent fringes can be most suited for tear film thickness measurement.

Figure 3:
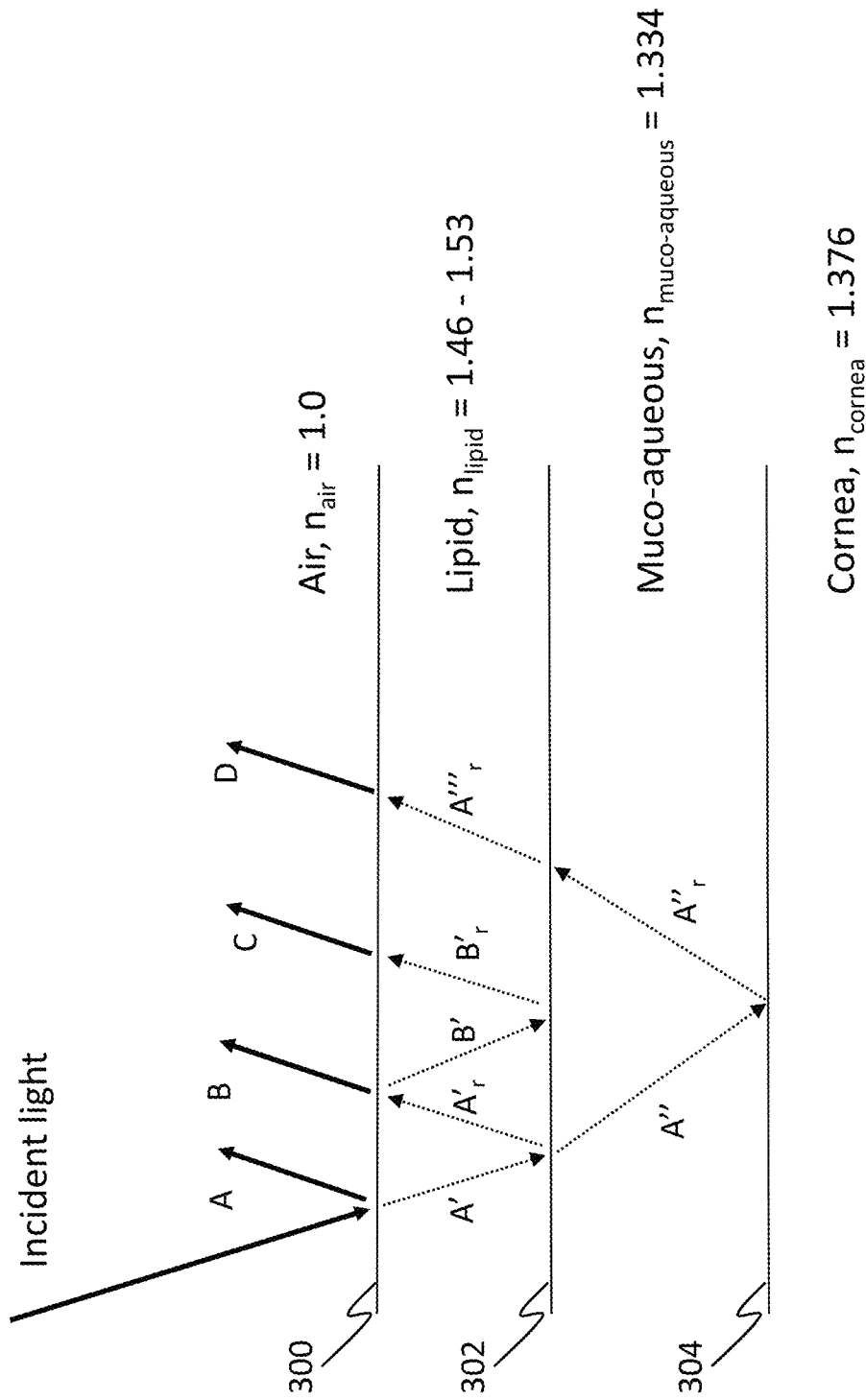
FIG. 3 illustrates transmission, reflection, and refraction of incident light through layers of the tear film.

More specifically, the transmission, reflection, and refraction for a light beam incident to the tear film is illustrated in with reference to FIG. 3. The resulting reflected rays of light from the incident beam are identified as rays A-D. The intensity for each pixel of a fringe image of the tear film is related to the thickness of each layer as follows.

According to Fresnel's equations, reflectance (R) and transmittance (T) at each layer interface is:

At the air-lipid interface 300:

$$R_{air\text{-}lipid} = \left|\frac{n_{lipid} - 1}{n_{lipid} + 1}\right| \text{ and } T_{air\text{-}lipid} = \sqrt{1 - R_{lipid}^2}$$

At the lipid-mucoaqueous interface 302:

$$R_{lipid\text{-}aqueous} = \left|\frac{n_{mucoaqueous} - n_{lipid}}{n_{mucoaqueous} + n_{lipid}}\right|$$

and $T_{lipid\text{-}aqueous} = \sqrt{1 - R_{mucoaqueous}^2}$

At the mucoaqueous-cornea interface 304:

$$R_{mucoaqueous\text{-}cornea} = \left|\frac{n_{cornea} - n_{mucoaqueous}}{n_{cornea} + n_{mucoaqueous}}\right|$$

and $T_{mucoaqueous\text{-}cornea} = \sqrt{1 - R_{cornea}^2}$ where $n_{lipid}$~1.46 to 1.53 and is the index of refraction of the lipid layer, $n_{aqueous}$~1.334 is and is the index of refraction of the muco-aqueous layer, and $n_{cornea}$~1.376 and is the index of refraction of the cornea.

From the above transmittance and reflectance determinations, an intensity factor for each beam A-D resulting from the incident light beam is:

$A = R_{air\text{-}lipid}$
$A' = T_{air\text{-}lipid}$
$A'_r = A' R_{lipid\text{-}mucoaqueous} = T_{air\text{-}lipid} R_{lipid\text{-}mucoaqueous}$
$A'' = A' T_{lipid\text{-}mucoaqueous} = T_{air\text{-}lipid} T_{lipid\text{-}mucoaqueous}$
$B = A_r' T_{air\text{-}lipid} = (T_{air\text{-}lipid})^2 R_{lipid\text{-}mucoaqueous}$
$B' = A_r' R_{air\text{-}lipid} = T_{air\text{-}lipid} R_{air\text{-}lipid} R_{lipid\text{-}aqueous}$
$A_r'' = A'' R_{mucoaqueous\text{-}cornea} = T_{air\text{-}lipid} T_{lipid\text{-}mucoaqueous} R_{mucoaqueous\text{-}cornea}$
$B_r' = B' R_{lipid\text{-}mucoaqueous} = T_{air\text{-}lipid} R_{air\text{-}lipid} (R_{lipid\text{-}mucoaqueous})^2$
$A_r''' = A_r'' T_{lipid\text{-}mucoaqueous} = T_{air\text{-}lipid} (T_{lipid\text{-}mucoaqueous})^2 R_{mucoaqueous\text{-}cornea}$
$C = B_r' T_{air\text{-}lipid} = (T_{air\text{-}lipid})^2 R_{air\text{-}lipid} (R_{lipid\text{-}mucoaqueous})^2$
$D = A_r''' T_{air\text{-}lipid} = (T_{air\text{-}lipid})^2 (T_{lipid\text{-}mucoaqueous})^2 R_{mucoaqueous\text{-}cornea}$ Substituting the known indices of refraction results in the following relative values for each ray of reflected incident light A, B, C, and D:

$A = R_{air\text{-}lipid}$~0.2
$B = (T_{air\text{-}lipid})^2 R_{lipid\text{-}mucoaqueous}$~$5.67 \times 10^{-2}$
$C = (T_{air\text{-}lipid})^2 R_{air\text{-}lipid} (R_{lipid\text{-}mucoaqueous})^2$~$6.69 \times 10^{-4}$
$D = (T_{air\text{-}lipid})^2 (T_{lipid\text{-}mucoaqueous})^2 R_{mucoaqueous\text{-}cornea}$~$1.49 \times 10^{-2}$ Further, the combined detected light wave of all reflected portions of the incident light (at wavelength λ and time t) can be written as:

$$U(\lambda, t) = A(\lambda)e^{i\left(\frac{2\pi c}{\lambda}t + \pi\right)} + B(\lambda)e^{i\left(\frac{2\pi c}{\lambda}t + \phi_1\right)} + C(\lambda)e^{i\left(\frac{2\pi c}{\lambda}t + \phi_2\right)} + D(\lambda)e^{i\left(\frac{2\pi c}{\lambda}t + \phi_3 + \pi\right)}$$

where $\phi_1 = \frac{4\pi n_{lipid} d_{lipid}}{\lambda}$, $\phi_2 = \frac{8\pi n_{lipid} d_{lipid}}{\lambda}$, and $\phi_3 = \frac{4\pi(n_{lipid} d_{lipid} + n_{mucoaqueous} d_{mucoaqueous})}{\lambda}$, where $d_{lipid}$ is the thickness of the lipid layer and $d_{mucoaqueous}$ is the thickness of the muco-aqueous layer, and where c is the speed of light.

According to one example based on Maxwell's equations, the reflectance intensity over time for each wavelength can thus be written as:

$I(\lambda) = \int U(\lambda,t)U^*(\lambda,t)dt \propto A^2 + B^2 + C^2 + D^2 - 2AB\cos(\phi_1) - 2AC\cos(\phi_2) + 2AD\cos(\phi_3) + 2BC\cos(\phi_2 - \phi_1) - 2BD\cos(\phi_3 - \phi_1) - 2CD\cos(\phi_3 - \phi_2)$ As shown above, A>>B~D>>C. Therefore, the above intensity equation can be simplified as:

$I(\lambda) \propto \alpha(\lambda) - \beta(\lambda)\cos(\phi_1) + \gamma(\lambda)\cos(\phi_3)$ where $\alpha(\lambda)$~$10^{-2}$ and $\beta(\lambda), \gamma(\lambda)$~$10^{-3}$. With substitution, the intensity of reflected light for a given incident light of wavelength λ:

$$I(\lambda) = \alpha(\lambda) - \beta(\lambda)\cos\left(\frac{4\pi n_{lipid} d_{lipid}}{\lambda}\right) + \gamma(\lambda)\cos\left(\frac{4\pi(n_{lipid} d_{lipid} + n_{mucoaqueous} d_{mucoaqueous})}{\lambda}\right) \quad \text{(Equation 1)}$$

As noted above, Equation 1 is based on Maxwell's equations. However, the particular model may be derived differently, such that a different equation representing intensity is solved for the layer thicknesses.

Regardless of the equation used to represent intensity, the actual measured intensity may be a summation of intensities for each incident wavelength in a given band of light from a light source (e.g., a discrete narrow band as discussed in more detail below). In the example where the measurement is performed for a band having wavelengths between $\lambda_1$ and $\lambda_2$, the measured intensity can be summarized as:

$$I_{measure}(\lambda_1, \lambda_2) = \int_{\lambda_1}^{\lambda_2} I(\lambda) E_{optics}(\lambda) E_{sensor}(\lambda) \quad \text{(Equation 2)}$$

where $I(\lambda)$ is an equation representing a measured intensity at a particular wavelength λ, $E_{optics}(\lambda)$ is the spectral response of the optical system used to pass the incident and reflected lights, and $E_{sensor}(\lambda)$ is the spectral response of a light sensor that detects the reflected light—in other words, the imaging sensor and system characteristics. In other embodiments, summation over wavelengths within each band can be used to determine an intensity for each band (that may be used to solve for layer thicknesses), without necessarily accounting for the spectral responses of the optical system and/or the sensor.

With the above model (summarized by Equations 1 and 2), the distances $d_{lipid}$ and $d_{mucoaqueous}$ of the lipid and muco-aqueous layers, respectively, can be determined for a detected intensity of reflected light, given a known wavelength of incident light and index of refraction. In this example with only two unknown variables, $d_{lipid}$ and $d_{mucoaqueous}$, theoretically only two independent intensity measurements are required to solve for those variables. Of course, in practice, more measurements can be performed. Additionally, more layers can be solved for producing equations of a similar form to Equations 1 and 2. The analysis to determine an optimal solution to the system of equations (a system of Equation 1 for each of a plurality of wavelengths of incident light) can be performed using, for example, least square fitting techniques, or a global optimization with pre-determined lookup table(s) (LUT). Using a least square fitting technique is dynamic and more dependent on initial conditions; but therefore prone to be trapped to local optimums. Using prior knowledge of the search range, lookup tables are more likely to produce a global optimal solution. Of course, a similarly simplified model or a more rigorous solution based on Maxwell's equations may also be used herein. And more sophisticated processing techniques, for example machine learning, can also be employed. For example, with a machine learning system, an algorithm can be trained to predict the thickness of the different layers using only $I_{measure}$ and without the knowledge of Equation 1. The training of the system can be performed in a supervised learning setting where pairs of $I_{measure}$ and the true thicknesses are available. It is noted that depending on the design of the machine learning system, the pair of $I_{measure}$ and the true thickness can be obtained in multiple ways, including measurement based on fully resolved spectrometric reflectance, and/or measurement of physical tear film model(s), and/or numerical modeling/simulation.

The present disclosure is also based in part on the recognition that RGB images are under-sampled and averaged spectrometric measurements. Therefore, traditional RGB fringe images are not adequate for thickness measurement for various layers of the tear film. However, measurement contrast can be enhanced with thickness information better preserved with narrower spectral bandwidths than traditional RGB color. In other words, the present disclosure also relates the imaging with narrow spectral bands—measuring intensity $I(\lambda)$ of Equation 1 and/or $I_{measure}(\lambda_1,\lambda_2)$ of Equation 2 for wavelengths of incident light in discrete narrow spectral bands (between $\lambda_1$ and $\lambda_2$).

Conventionally, the muco-aqueous layer has only been able to be measured at a single spot with broadband white light source based on spectrometry technology. However, using a smaller number of spectral bands and a narrower spectral bandwidth than conventional RGB imaging can provide sufficient signal strength for 2D muco-aqueous layer thickness measurement. Further, narrow spectral bandwidths can help to enhance the imaging contrast, particularly for muco-aqueous layer measurement; although, if the bandwidth is too narrow, system tolerance may be adversely affected.

Such narrow spectral band imaging can be achieved by selecting an appropriate light source, and/or spectral filters to generate those narrow spectral bands. Relative to broadband imaging, the use of narrow spectral bands further enhances the contrast for muco-aqueous layer thickness measurement by mitigating the washout effect and preserving thickness information for the thickest layer in the multilayer structure. More particularly, the washout effect occurs when, with reference to Equation 2, $\lambda_1$ and $\lambda_2$ are significantly different and thus $I_{measure}(\lambda_1, \lambda_2)$ is integrated over a large range. As a result, the uniqueness of each intensity measured at the individual wavelengths $I(\lambda)$ (and caused by different layer thicknesses) is minimized (effectively "washed out") by the large integration range. This can ultimately cause different layer thicknesses to generate the same value for $I_{measure}(\lambda_1, \lambda_2)$. Practically, the minimum bandwidth is determined by measurement SNR, performance tolerance, and cost. And the maximum bandwidth is determined by the thickest layer in the structure and the system response characteristics, particularly the sensitivity/dynamic range of the sensors. Considering this, a preferable bandwidth for the discrete narrow spectral bands is between a few nanometers to a few tens of nanometers (at full width, half maximum), but may be a hundred nanometers or greater if any of the features of such bands described herein are achieved.

It is also noted that the spectral bandwidth affects measurement accuracy differently for the lipid layer and muco-aqueous layer. Instead of a tradeoff bandwidth that potentially compromises the performance for all layers, the use of a plurality of narrow spectral bandwidths makes it possible to optimize a set of spectral bands with different bandwidths for a particular layer thickness measurement.

The spectral bands can be distributed across the entire spectral bandwidth in any fashion. For instance, they can be evenly distributed. In other embodiments, the spectral bands can be distributed to take advantage of the emission spectral bands of the light source or the quantum efficiency of a detector of the reflected light. In still other embodiments, the spectral bands can be distributed to provide maximum measurement sensitivity/accuracy based on a prior knowledge of the thickness ranges for different layers.

When combined with the above analysis of the measurement data (solving a system of equations for a plurality of measured intensities of reflected light), the measurement speed/efficiency can be significantly enhanced with a few spectral bands (depending on the number of layers to be measured), thereby overcoming the deficiencies of other spectrometer based methods with hundreds of spectral channels. For example, the improved measurement efficiency can help to increase measurement speed and/or reduce illumination power and improve user experience, which can further help to improve measurement performance. It is noted that such an approach does not depend on specific requirement for system/operating parameters (e.g., the center wavelength and the bandwidth for each spectral band); and these parameters may be set based on the statistical distribution of tear film thicknesses. Nevertheless, calibration of the system based on selected parameters may still be performed.

For thickness measurement of the tear film, the tear film can be modeled as two primary layers: the lipid layer and the muco-aqueous layer. Thus theoretically for a two layer thickness measurement, as few as two spectral bands are sufficient to derive the thickness for both layers. However, the number of spectral bands can be higher to improve measurement reliability and accuracy. Compared with the full spectrum spectrometry measurement, fewer spectral bands improves detection efficiency and the number of photons per spectral band can be much higher to achieve a better signal-to-noise ratio (SNR).

Figure 4:
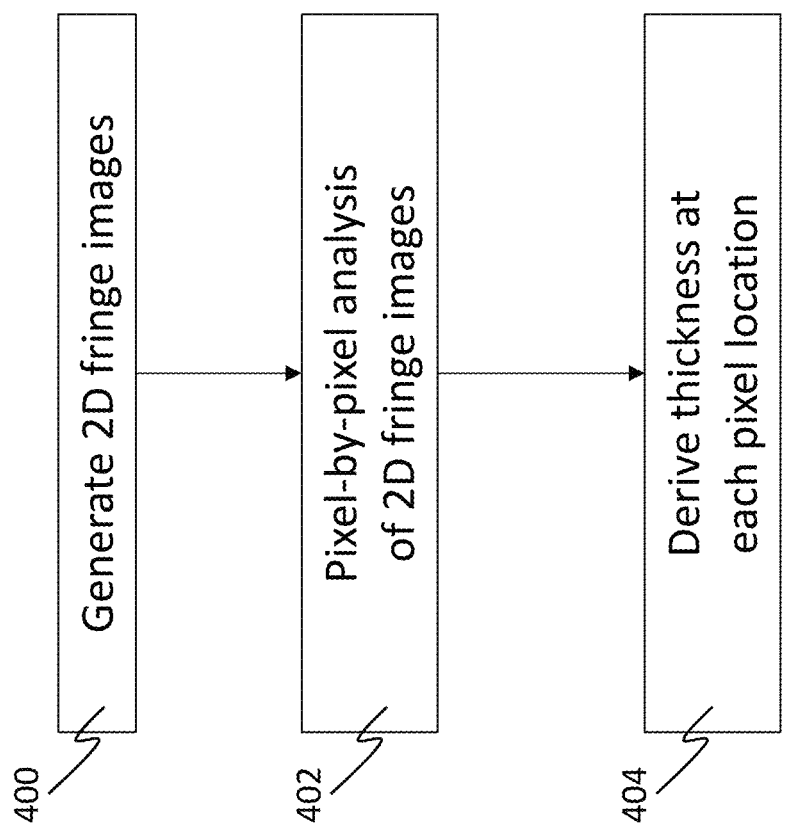
FIG. 4 illustrates a flow chart of the operation of the system and method herein.

In view of these recognitions, briefly the system and method described herein operate according to the flow chart in FIG. 4. First 2D fringe images of the tear film of the eye are generated 400 for each of a plurality of spectral bands (e.g., from discrete narrow spectral band spectrometry) of incident light on the eye. The resulting 2D images are analyzed 402 on a pixel-by-pixel basis to determine the intensity of the reflected light at each wavelength at that pixel. The thickness of each layer for a location on the eye/tear film corresponding to each pixel is then derived 404 from the intensity based on the above, or a similar, model, by substituting the determined intensities and wavelengths in Equation 1 and 2, and solving the resulting system of equations for the different layer thicknesses.

Figure 5:
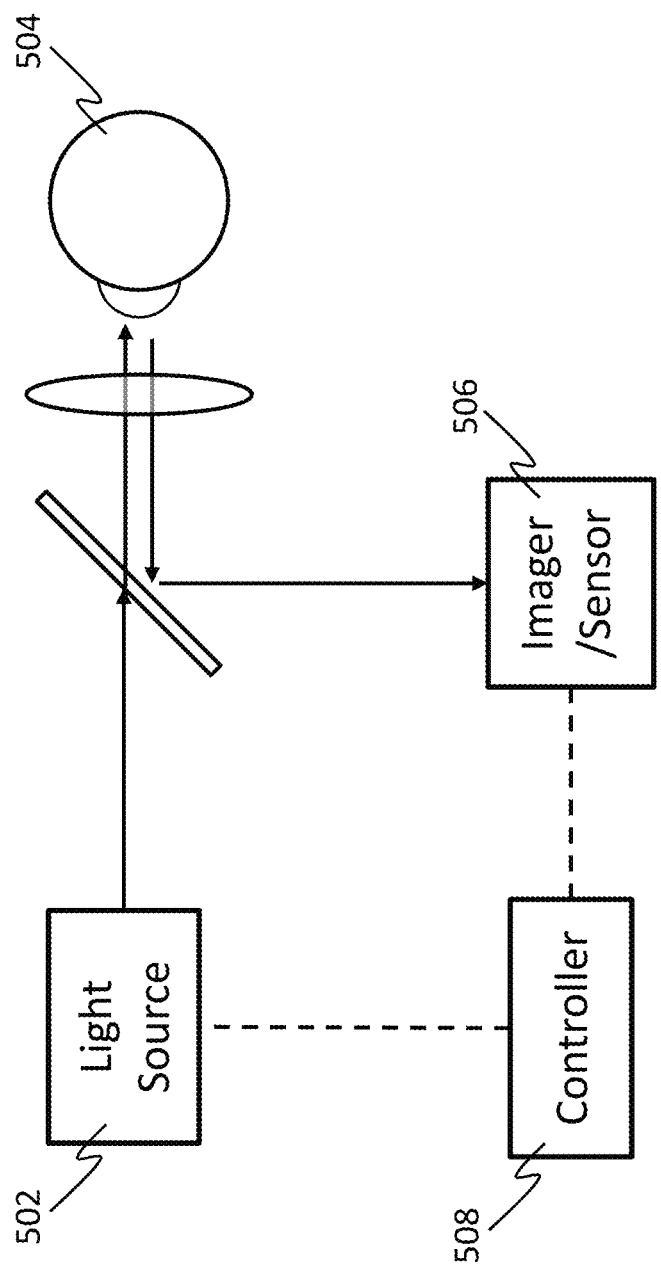
FIG. 5 is an example schematic of a system for generating 2D fringe images.

With reference to FIG. 5, a system, similar to an interferometric imaging system, for generating 2D fringe images is described. Therein, incident light is generated from a light source 502 or other illumination and source optics. The incident light beam is directed to an object to be imaged (e.g., the tear film of a subject's eye 504). Light rays reflected by the object are then detected by an imager or optical sensor 506 or like photodetector. The output of the photodetector is then supplied to a computer 508 or like processor (e.g., controller or other CPU) for further processing and analysis. The light source 502 and imager or optical sensor 506 are preferably synchronized. This synchronization may be coordinated directly between the source 502 and imager or optical sensor 506, or facilitated by processing at the computer 508.

As noted above, the incident light is generated, and the reflections from the object are detected, in a plurality of discrete narrow spectral bands. These discrete narrow spectral bands do not practically have a lower bandwidth limit and may be as great as hundreds of nanometers (at full width, half maximum) if any of the features of such bands described herein are achieved. Preferably, the spectral bands do not overlap, however, in some embodiments the bands may be partially overlapping. According to one non-limiting example, the discrete narrow spectral bands may be between 5 nm and 100 nm; and according to another non-limiting example may be about 40 nm. According to one example, illustrated in FIG. 6, imaging may be conducted with five bands between about: 1) 425-475 nm, 2) 500-550 nm, 3) 650-700 nm, 4) 750-800 nm, and 5) 950-1000 nm. According to another example, each band is centered at 400 nm, 500 nm, 600 nm, 700 nm, and 800 nm.

Figure 7:
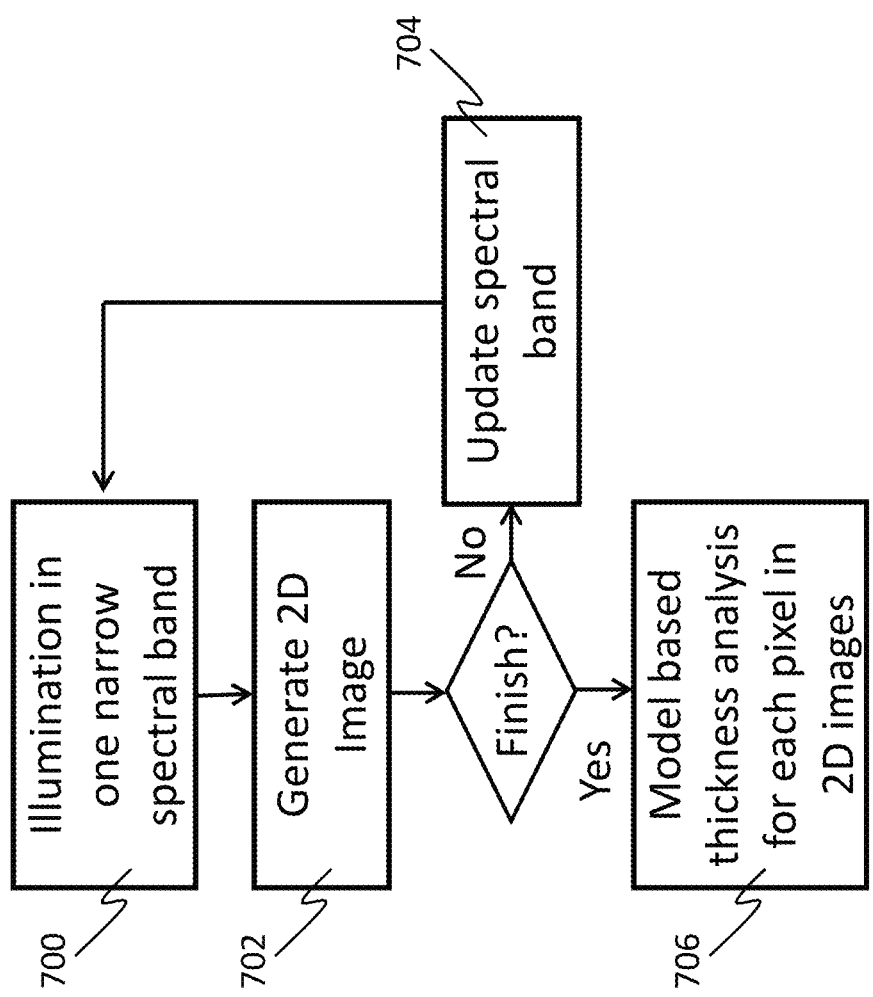
FIG. 7 illustrates a first example imaging/measurement method.
Figure 8:
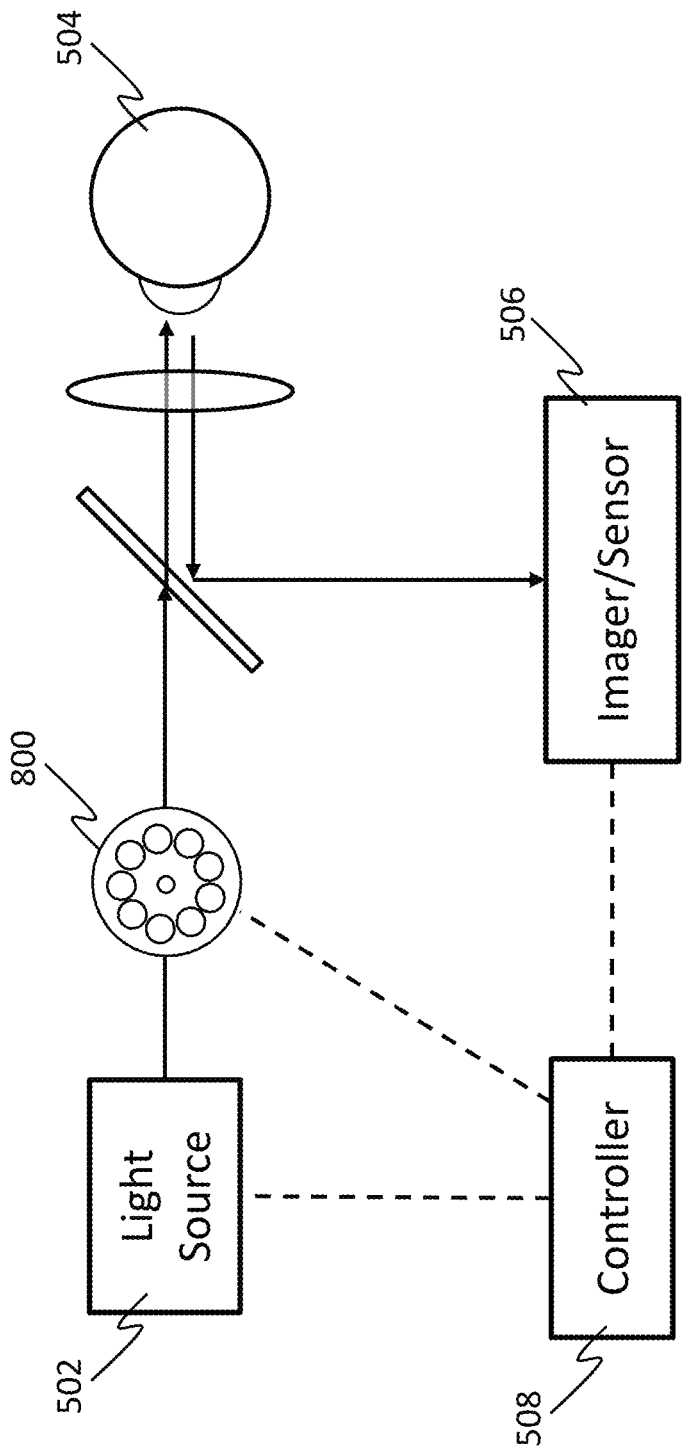
FIG. 8 illustrates a first example imaging/measurement system.

This incident light may be generated and detected according to any number of embodiments. For example, a first embodiment is illustrated in FIGS. 7 and 8. Therein, the light source 502 sequentially generates and detects light in each desired band. This can be accomplished, for example, by generating a broad bandwidth light at the light source 502 and sequentially applying different filters 800 (e.g., via a filter wheel) so that only the desired narrow bandwidth of light is provided to the eye at any given time. Alternatively, the light source 502 itself may generate light only in the desired narrow spectral band.

In other words, the eye is first illuminated 700 in a first of the narrow spectral bands and then an entire 2D image for the first band is generated 702. Illumination 700 and acquisition 702 is then repeated for each of the narrow spectral bands. To update the band 704, for example, the processor 508 may control which filter 800 is aligned with the light source 502 or control the light source 502 to output a different narrow spectral band. After all 2D images have been generated, thicknesses are determined 706 for locations of the eye corresponding to each pixel of the 2D images based on the above-described model.

Figure 9:
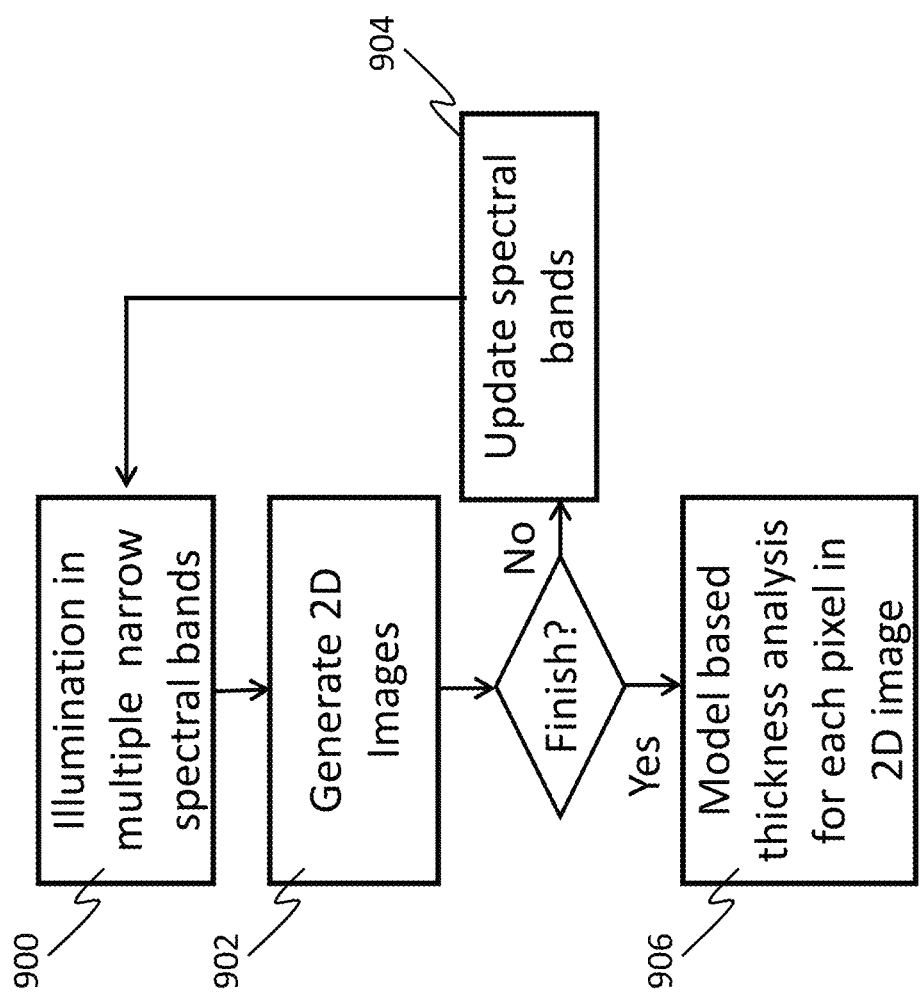
FIG. 9 illustrates a second example imaging/measurement method.
Figure 10:
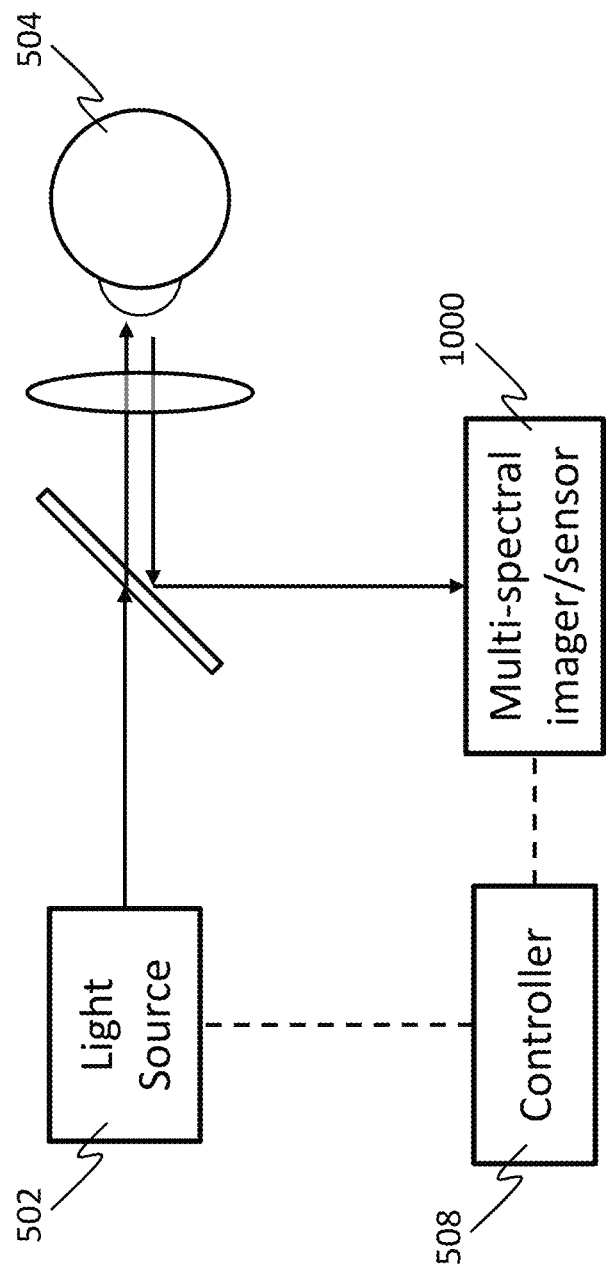
FIG. 10 illustrates a second example imaging/measurement system.

Another embodiment based on a parallel acquisition of 2D images is illustrated in FIGS. 9 and 10. There, the light source 502 generates light 900 in a plurality of narrow spectral bands simultaneously. Accordingly, reflected light is detected by, for example, a multi-channel/multi-band 2D camera/sensor array 1000. Multi-spectrum optics and sensors, such as a prism-based multi-chip camera or a multi-layer sensor chip may be used to detect light in the multiple narrow spectral bands. With these, multiple spectral bands can be detected at the same time. Such detection can help reduce motion artifacts. After detection, 2D images are generated 902 for each of the detected narrow spectral bands. If fewer than all of the narrow spectral bands were generated by the light source 502, the illumination 900 and 2D image generation 902 is repeated (by updating the light source 904 as described above and repeating illumination 900 and 2D image generation 902) until there are 2D images for all desired narrow spectral bands. After all 2D images have been generated, thicknesses are determined 906 for locations of the eye corresponding to each pixel of the 2D images based on the above-described model.

In variations of the above embodiments, incident light is generated and reflected rays are detected (either by adjusting the narrow spectral band of incident light, or detecting multiple spectrums of light) for all desired narrow spectral bands at a single location of the eye. Imaging progresses location by location until data for all pixels of the 2D images has been acquired. All 2D images are then generated after illumination and detection has been completed. In other words, illumination and detection is repeated for each pixel location until the entire imaging region has been imaged and each 2D image acquired. Then, the thickness of each layer is determined as above.

In still another embodiment, the above sequential and parallel methods may be combined. For instance, illumination may be composed of light in multiple spectral bands at one moment and changed to different multi-spectral bands at the next moment, with the illumination synchronized accordingly with the multi-channel sensor/camera.

While system designs based on the above-described features perform efficiently with minimal waste of reflected light, it is possible to implement a less efficient system with a simpler design that may still meet safety criteria. For instance, in still another embodiment, the light source 502 may be a broadband (continuous or discrete) light source for illumination and the imager or optical sensor 506 may be a hyperspectral/multispectral imaging camera (where a cluster of pixels are coated with filters for different spectral band, similar to RGB color cameras using Bayer filter). While overall imaging efficiency may not be as optimal, the thickness measurement can still be performed, for example, based on the above model. Similarly, other hyperspectral/multi-spectral imaging technologies can be adopted to achieve thickness measurement, at the cost of overall system efficiency.

As suggested above, for any embodiment, the light source 502 may emit light of the different spectral bands by using multiple sub light sources, by sweeping/wavelength hopping, or by using a broadband light source combined with optical filters. It is estimated that the illumination power for reliable measurement is less than 100 μW. The light source 502 can thus be any type (or combination of types) of light source capable of producing multiple spectral bands. For example, the light source 502 may be a broadband light source like a thermal source and a halogen lamp, or LED(s). In other embodiments, a synthesized white light source with spectral bands matching a color camera can be employed for measuring spectral bands in parallel. Additional synthesized white light sources (with different set of spectral bands) can also be employed to increase the effective number spectral bands.

For any embodiment, the camera/sensor photodetector 506 for detecting the reflected light may be selected based on the sensitivity and color imaging mechanism of the camera/sensor. For example, while traditional RGB cameras could be used, they commonly include Bayer filters, which limit the camera's efficiency and spatial displacement for pixels at different spectral bands. Alternatively prism based/multi-layer sensor multi-channel cameras offer better efficiency and resolution.

While FIGS. 8 and 10 illustrate the incident light beam illumination source/optics separately from the imaging optics/sensor for detecting reflected light, it is understood that these could be integrated into a single device. In any event, the generation of the incident light and detection of the reflected light are synchronized as needed.

Simulation and Test Results

Figure 11A:
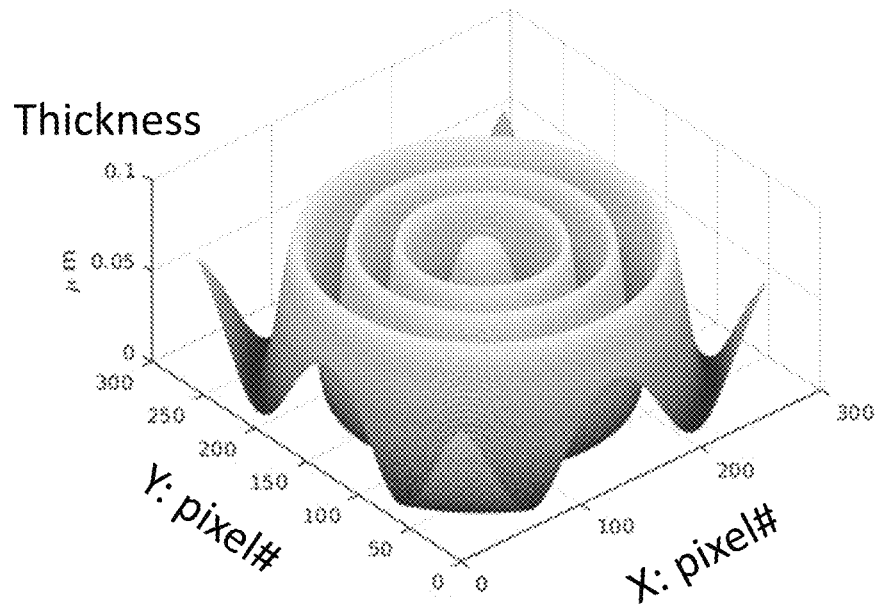
FIG. 11A illustrates a thickness pattern for a 2D area of an outmost layer of a simulated model having a refraction index of the human lipid layer.
Figure 11B:
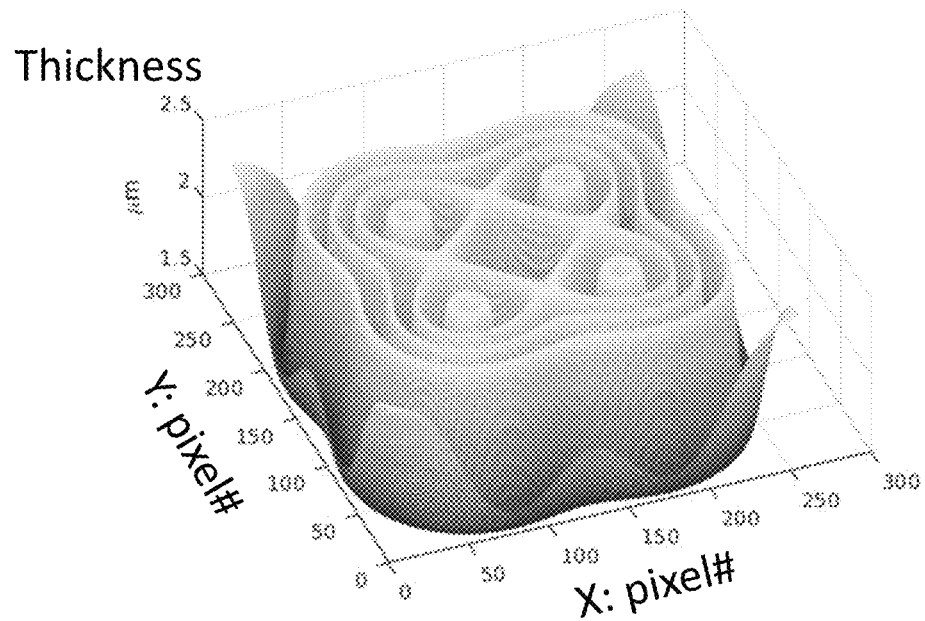
FIG. 11B illustrates a thickness pattern for a 2D area of a middle layer of the simulated model having a refraction index of the human muco-aqueous layer.
Figure 12A:
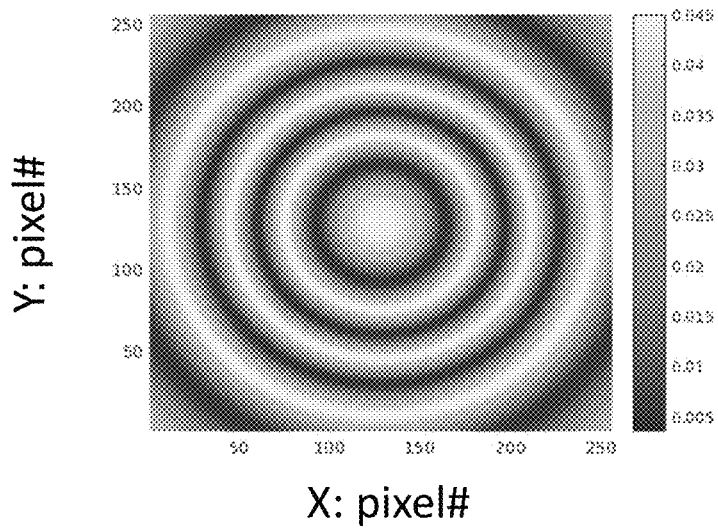
FIG. 12A is a reconstructed thickness map for the outmost layer of FIG. 11A using the method described herein.
Figure 12B:
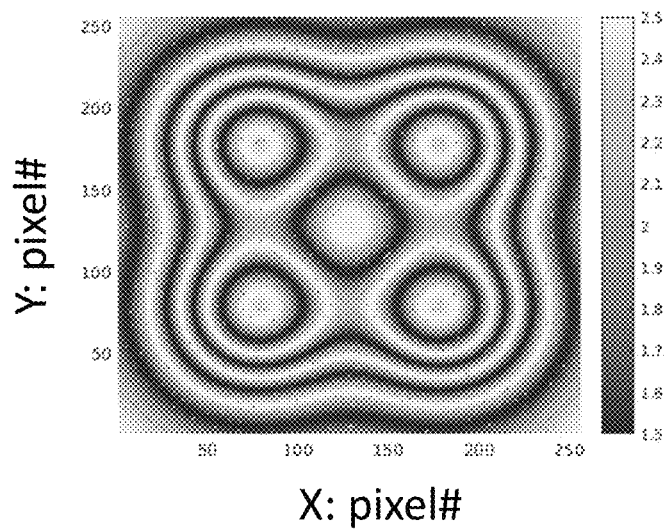
FIG. 12B is a reconstructed middle layer thickness map of FIG. 11B using the method described herein.

FIGS. 11 and 12 illustrate a simulation and results according to the above-described method. More particularly, a simulated model of a three layer structure was generated with a refractive index of the top layer set to correspond to that of the human lipid layer and a refractive index of the middle layer set to correspond to that of the human muco-aqueous layer. FIG. 11A illustrates a thickness map of the top layer of the simulated model and FIG. 11B illustrates a thickness map of the middle layer of the simulated model. Although not representative of actual tear film layer thicknesses, the simulated thickness maps shown in FIGS. 11A and 11B were generated with thickness ranges of a typical human tear film. Given the above, the simulated model in FIGS. 11A and 11B facilitated testing of a range of thicknesses of an actual tear film and the visualization of results (shown in FIGS. 12A and 12B).

Using discrete narrow spectral bands (having a 40 nm bandwidth and centered around 400 nm, 500 nm, 600 nm, 700 nm, and 800 nm) using the above-described model, the simulated lipid layer thickness map of FIG. 11A and simulated muco-aqueous layer thickness map of FIG. 11B were reconstructed. These reconstructions are illustrated in FIGS. 12A and 12B, respectively. As can be seen, the 2D reconstructed maps of FIGS. 12A and 12B closely mirror the simulated maps of FIGS. 11A and 11B. Therefore, it is understood that the above-described model can properly be used to determine layer thicknesses of the tear film by imaging the tear film with discrete narrow spectral bands.

According to another experimental test, a three-layer structure was formed of a ~60 nm silicon dioxide ($SiO_2$) top layer, a ~1 μm magnesium fluoride ($MgF_2$) intermediate layer, and a >1 mm BK7 borosilicate glass substrate layer. This structure was imaged and analyzed according to the above method using five discrete narrow spectral bands and a lookup table to determine the optimal solutions to the system of equations (of Equations 1 and 2). While Equations 1 and 2 specifically reference the indices of refraction and depths of the lipid and muco-aqueous layers, it is understood that the corresponding variables represent the silicon dioxide and magnesium fluoride layers of the structure in this experiment.

Figure 6:
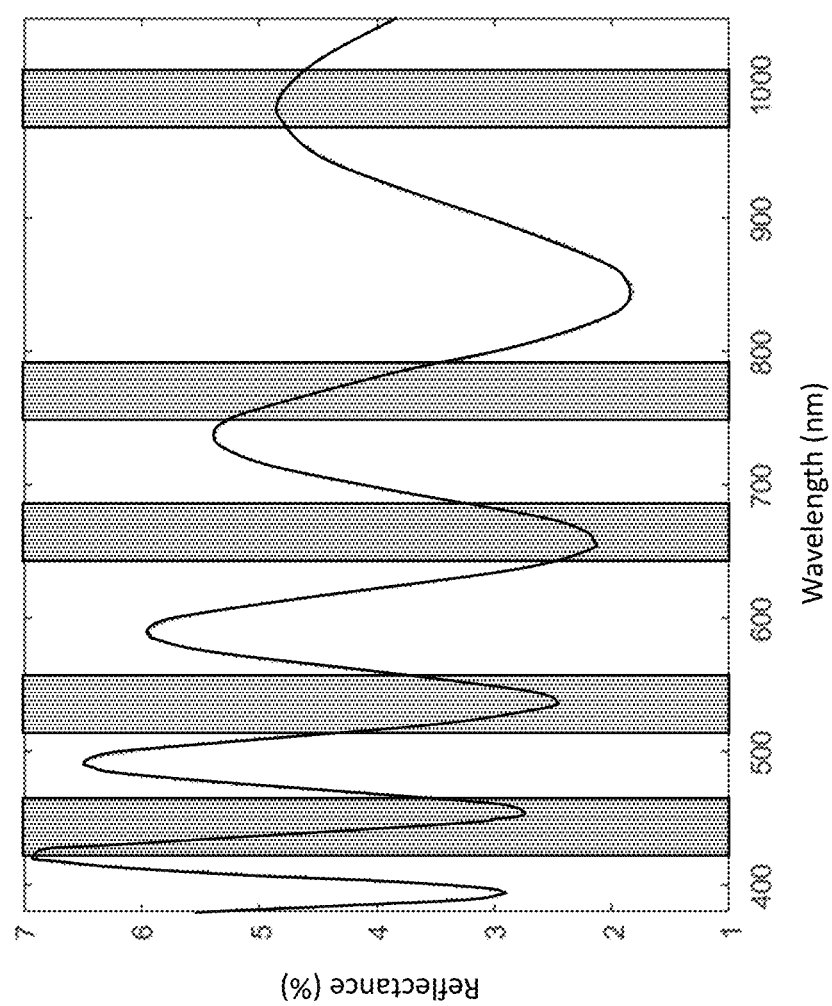
FIG. 6 illustrates a conceptual representation of discrete narrow spectral bands used with the system and method described herein, in comparison with the fully resolved spectrometric reflectance measurement.

In this test, imaging was performed with the spectral bands that were evenly distributed (e.g., as in the above example with 40 nm bands centered at 400, 500, 600, 700, and 800 nm) and unevenly distributed (e.g., as illustrated in FIG. 6) across the full spectrum of the imaging system's light source. Using collected data from imaging with evenly distributed narrow spectral bands to form a system of equations (of Equation 1), the thickness of the $SiO_2$ layer was estimated to be 56.5 nm and the thickness of the $MgF_2$ layer was estimated to be 1 μm. Similarly, when imaging with discrete narrow spectral bands that were unevenly distributed, the thicknesses were estimated to be 55.0 nm and 1 μm, respectively. A conventional curve fitting technique estimated the layers to be 56.2 nm and 1 μm, respectively. Accordingly, the method and system described herein is capable of producing similarly accurate results to the conventional approach, but without the above-noted deficiencies.

While various features are presented above, it should be understood that the features may be used singly or in any combination thereof. Further, it should be understood that variations and modifications may occur to those skilled in the art to which the claimed examples pertain. Similarly, while the above disclosure primarily relates to imaging of the tear film of an eye, the disclosure may also be applied to imaging and determining layer thicknesses for any other multilayer structure.

It is also noted that any of the aspects or combination of aspects described above may be implemented via hardware or software. For example, these aspects may be implemented on a processor or a plurality of processors, such as a graphics processing unit (GPU) or similar dedicated graphics processor. These processor(s) also may be embedded or integrated with other processors designed for a separate purpose, for example, as part of a central processing unit (CPU). Additionally, the processor (and processing thereon) may be independent of or integrated with any system (e.g., including a light source, photodetector, and optics) used for performing and controlling imaging of the tear film.

What is claimed is:

1. A method for measuring layer thicknesses of a multilayer structure comprising:
    generating a first two-dimensional (2D) image of the structure by, for each pixel of the first 2D image, measuring an intensity of a reflection of a first incident light at a location of the structure corresponding to the pixel;
    generating a second 2D image of the structure by, for each pixel of the second 2D image, measuring an intensity of a reflection of a second incident light at a location of the structure corresponding to the pixel;
    determining a thickness for at least one layer of the structure at each location of the structure based on the intensities of the measured reflections of corresponding pixels in the first and second 2D images,
    wherein the first incident light is generated in a first discrete narrow spectral band, the second incident light is generated in a second discrete narrow spectral band, and the first and second discrete narrow spectral bands do not fully overlap, and
    wherein the intensities of the reflection of the first and second incident light are measured by a light sensor.

2. The method of claim 1, wherein the first and second discrete narrow spectral bands are sufficiently narrow to mitigate fringe washout and preserve thickness information of the thickest layer of the structure.

3. The method of claim 1, wherein the multilayer structure is a tear film of an eye.

4. The method of claim 1, further comprising generating additional 2D images with incident light in additional discrete narrow spectral bands, wherein a total number of narrow spectral bands is equal to or greater than a number of determined layer thicknesses.

5. The method of claim 1, wherein the at least one determined layer thickness is a thickness of a lipid layer or a muco-aqueous layer of a tear film of an eye.

6. The method of claim 1, further comprising generating a third 2D image with incident light in a third discrete narrow spectral band, wherein the first, second, and third discrete narrow spectral bands are evenly distributed across a spectral bandwidth of measurement.

7. The method of claim 1, further comprising generating a third 2D image with incident light in a third discrete narrow spectral band, wherein the first, second, and third discrete narrow spectral bands are unevenly distributed across a spectral bandwidth of measurement.

8. The method of claim 1,
    wherein the thickness for the at least one layer of the structure is determined by solving a system of equations for layer thickness of the at least one layer of the structure, and wherein each of the equations represents a measured intensity of reflected light from incident light on the structure at wavelengths corresponding to the first and second discrete narrow spectral bands, and is further a function of indices of refraction for the at least one layer of the structure.

9. The method of claim 8, wherein the measured intensity of reflected light is determined according to the following equation:

$$I(\lambda) = \alpha(\lambda) - \beta(\lambda)\cos\left(\frac{4\pi n_1 d_1}{\lambda}\right) + \gamma(\lambda)\cos\left(\frac{4\pi(n_1 d_1 + n_2 d_2)}{\lambda}\right)$$

wherein $\lambda$ represents wavelength within the first or second discrete narrow spectral band, $\alpha$, $\beta$, and $\gamma$ are predetermined factors, $n_1$ and $n_2$ are the indices of refraction for first and second layers of the structure, respectively, and $d_1$ and $d_2$ are the layer thicknesses for the first and second layers of the structure, respectively.

10. The method of claim 8, wherein at least one of the measured intensities is adjusted for a spectral response of an optical system that provides the first and second incident lights to the structure and light reflected by the structure to the light sensor, or for a spectral response of the light sensor.

11. The method of claim 1,
wherein the thickness for the at least one layer of the structure is determined by solving a system of equations for layer thickness of the at least one layer of the structure, each of the equations representing a summation of measured intensities of reflected light from incident lights on the structure at wavelengths corresponding to the first and second discrete narrow spectral bands determined according to:

$I_{measure}(\lambda_1,\lambda_2) = \int_{\lambda_1}^{\lambda_2} I(\lambda) E_{optics}(\lambda) E_{sensor}(\lambda)$ wherein:
 $I(\lambda)$ is a measured intensity of reflected light for an incident wavelength of light $\lambda$, and is further a function of the layer thickness of the at least one layer of the structure, and the indices of refraction for the at least one layer of the structure,
 $\lambda_1$ and $\lambda_2$ are lower and upper limits for a respective one of the discrete narrow spectral bands,
 $E_{optics}$ is a spectral response of an optical system that provides the first and second incident lights to the structure and light reflected by the structure to the light sensor, and $E_{sensor}(\lambda)$ is a spectral response of the light sensor.

12. The method of claim 1, wherein the thickness for the at least one layer of the structure is determined by inputting a measured intensity of reflected light from incident light on the structure to a trained machine learning system.

13. The method of claim 12, wherein the machine learning system is trained in a supervised setting to output a thickness to relate a measured intensity to a layer thickness based on fully resolved spectrometric reflectance for a wavelength of incident light corresponding to the measured intensity, measurements of a physical tear film model, and/or numerical models or simulations.

14. The method of claim 1, wherein the locations of the structure corresponding to each pixel of the first and second 2D images are illuminated with the first incident light prior to the locations of the structure corresponding to each pixel of the first and second 2D images being illuminated with the second incident light.

15. The method of claim 1, wherein the location of the structure corresponding to a first pixel of the first and second 2D images is illuminated with the first incident light and the second incident light prior to the location of the structure corresponding to a second pixel being illuminated with the first incident light and the second incident light.

16. The method of claim 1, wherein for each location of the structure corresponding to a pixel of the first and second 2D images, the pixel location is illuminated with the first and second incident light simultaneously and the intensities of the reflections of the first and second incident lights are measured simultaneously.

17. The method of claim 1, wherein the first and second discrete narrow spectral bands do not overlap.

18. The method of claim 1, wherein a bandwidth of the first discrete narrow spectral band and is different than a bandwidth of the second discrete narrow spectral band.

19. An imaging system comprising:
 a processor configured to control execution of the steps of the method of claim 1;
 a light source configured to generate the first and second incident light; and
 the light sensor configured to measure the reflection of incident light.

20. The imaging system of claim 19, wherein the light source is a broadband light source or a light emitting diode.

21. The imaging system of claim 19, wherein the light sensor is a hyperspectral/multi-spectral camera.

* * * * *